United States Patent
Tsai et al.

(10) Patent No.: US 9,364,846 B2
(45) Date of Patent: Jun. 14, 2016

(54) CIRCUIT FOR LIQUID ATOMIZING DEVICE AND DEVICE THEREOF

(71) Applicant: HCMED INNOVATIONS CO., LTD., Taipei (TW)

(72) Inventors: Wen-Yu Tsai, Taipei (TW); Chieh-Sheng Cheng, Taipei (TW)

(73) Assignee: HCMED INNOVATIONS CO., LTD., Taipei (TW)

(*) Notice: Subject to any disclaimer, the term of this patent is extended or adjusted under 35 U.S.C. 154(b) by 59 days.

(21) Appl. No.: 14/532,159

(22) Filed: Nov. 4, 2014

(65) Prior Publication Data

US 2016/0030966 A1 Feb. 4, 2016

(30) Foreign Application Priority Data

Aug. 1, 2014 (TW) .............................. 103126376 A (51) Int. Cl.
| | |
|---|---|
| *B05B 1/08* | (2006.01) |
| *B05B 3/04* | (2006.01) |
| *B05B 17/06* | (2006.01) |
| *A61M 11/00* | (2006.01) |

(52) U.S. Cl.
CPC .......... *B05B 17/0653* (2013.01); *A61M 11/005* (2013.01); *A61M 2205/0294* (2013.01); *A61M 2205/33* (2013.01)

(58) Field of Classification Search
CPC .... B05B 17/06; B05B 17/0607; B05B 11/30; B05B 7/2405

USPC ............................................ 239/102.1, 102.2
See application file for complete search history.

(56) References Cited

U.S. PATENT DOCUMENTS

| | | | | |
|---|---|---|---|---|
| 2008/0302651 | A1* | 12/2008 | Arai ....................... | C02F 1/4602 204/157.15 |
| 2014/0042032 | A1* | 2/2014 | Shimoyama ............. | C25D 5/18 205/118 |

FOREIGN PATENT DOCUMENTS

| | | | | |
|---|---|---|---|---|
| JP | 11010154 | * | 1/1999 | .......... B05B 17/0607 |
| JP | 02009028598 A | * | 2/2009 | .......... B05B 17/0607 |

* cited by examiner

*Primary Examiner* — Davis Hwu
(74) *Attorney, Agent, or Firm* — Li & Cai Intellectual Property (USA) Office (57) ABSTRACT

A circuit for liquid atomizing device coupled to an atomizing module is disclosed. The circuit for liquid atomizing device includes a conversion unit, a control unit and a voltage adjustment unit. The control unit is coupled to the conversion unit and controls the conversion unit to output a transforming voltage. The voltage adjustment unit is coupled between the conversion unit and the atomizing module. The voltage adjustment unit according to the transforming voltage outputs a driving voltage to the atomizing module. The driving voltage includes a plurality of electrolysis sections and a plurality of negative level sections. Each electrolysis section indicates that the atomizing module produces a forward electrolysis reaction. Each negative level section indicates that the atomizing module produces a backward electrolysis reaction.

10 Claims, 6 Drawing Sheets

CIRCUIT FOR LIQUID ATOMIZING DEVICE AND DEVICE THEREOF

BACKGROUND

1. Technical Field

The present disclosure relates to a circuit for liquid atomizing device and device thereof, in particular to a circuit for liquid atomizing device having an extended usage life, and a device thereof.

2. Description of Related Art

A liquid atomizing device is widely applied in many fields already, such as application of lowering temperature, increasing humidity, damping dust, and medicine, etc. For example, when being applied in a breathing medical equipment, the liquid atomizing device produces drugs having grain size lower than 3 μm~5 μm to ensure that the drug can reach the alveolus to be absorbed by human body, so as to improve treatment efficiency of the drug. In other example, when liquid atomizing device is applied in the agriculture for the purpose of lowering temperature in the greenhouse, the optimal diameter of the mist particle is 17 μm to form the mist having the most suitable concentration and effect of shielding light, so as to efficiently decrease the requirement of the cropper for irrigation.

At present, the vibration type liquid atomizing device drives a piezoelectric piece by frequency to form a sound wave oscillation and further to produce mist particles. For example, an atomizing module of the liquid atomizing device includes the piezoelectric piece. The piezoelectric piece has a positive electrode and a negative electrode, and is contacted with or immersed into the liquid to atomize the liquid. However, the verdigris or the electrolysis material is often produced and attached on the positive electrode and the negative electrode of the piezoelectric piece contacted with or immersed into the liquid. The piezoelectric piece producing the verdigris or being attached with the electrolysis material will impair the usage of the liquid atomizing device, so the usage life of the liquid atomizing device is reduced.

Moreover, in the prior art the piezoelectric piece is provided with the driving voltage by a voltage transformer, it causes more power consumption. For example, the voltage transformer needs 350 mA of electric power to drive the piezoelectric piece by frequency to form the sound wave oscillation. Therefore, it causes the inconvenient in using the liquid atomizing device.

SUMMARY

An exemplary embodiment of the present disclosure provides a circuit for liquid atomizing device and device thereof which utilizes a circuit design in which a voltage adjustment unit outputs a driving voltage including negative level sections, to enable the atomizing module to produce a backward electrolysis reaction. Therefore, the usage life and effect of the atomizing module can be improved.

According to one exemplary embodiment of the present disclosure, a circuit for liquid atomizing device is coupled to an atomizing module. The circuit for liquid atomizing device includes a conversion unit, a control unit and a voltage adjustment unit. The control unit is coupled to the conversion unit and controls the conversion unit to output a transforming voltage. The voltage adjustment unit is coupled between the conversion unit and the atomizing module. The voltage adjustment unit according to the transforming voltage outputs a driving voltage to the atomizing module. The driving voltage includes a plurality of electrolysis sections and a plurality of negative level sections. Each electrolysis section indicates that the atomizing module produces a forward electrolysis reaction. Each negative level section indicates that the atomizing module produces a backward electrolysis reaction.

The embodiment of the present disclosure provides a liquid atomizing device including a conversion unit, a control unit, a voltage adjustment unit and an atomizing module. The control unit is coupled to the conversion unit and controls the conversion unit to output a transforming voltage. The voltage adjustment unit is coupled between the conversion unit and the atomizing module. The atomizing module is coupled to the voltage adjustment unit and a ground end. The voltage adjustment unit according to the transforming voltage outputs a driving voltage to the atomizing module. The driving voltage includes a plurality of electrolysis sections and a plurality of negative level sections. Each electrolysis section indicates that the atomizing module produces a forward electrolysis reaction. Each negative level section indicates that the atomizing module produces a backward electrolysis reaction.

In practice, the present disclosure utilizes the circuit design of the voltage adjustment unit in the circuit for liquid atomizing device to produce the forward electrolysis reaction or the backward electrolysis reaction according to an electrolysis section or a negative level section of the driving voltage, to prevent the electrolysis material from attaching on the atomizing module, so that the usage life of the atomizing module can be elongated.

In order to further understand the techniques, means and effects of the present disclosure, the following detailed descriptions and appended drawings are hereby referred, such that, through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DESCRIPTION OF THE EXEMPLARY EMBODIMENTS

Reference will now be made in detail to the exemplary embodiments of the present disclosure, examples of which are illustrated in the accompanying drawings. Wherever possible, the same reference numbers are used in the drawings and the description to refer to the same or like parts.

Figure 1:
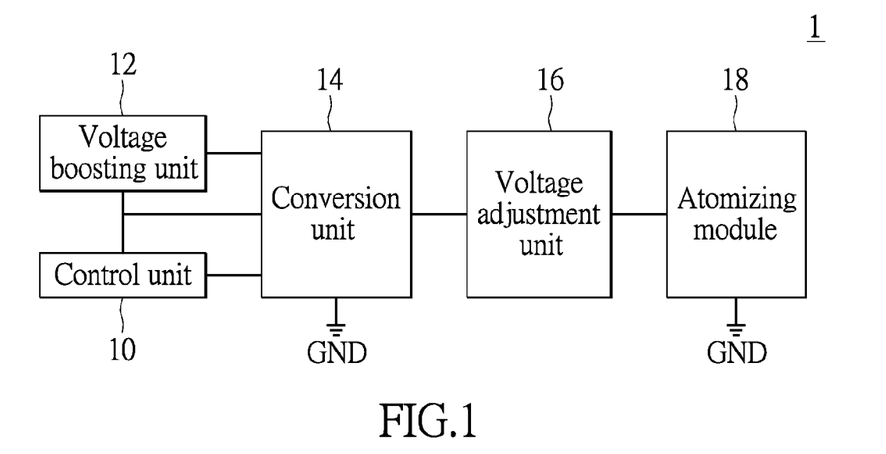
FIG. 1 is a function block diagram of a circuit for liquid atomizing device of an embodiment of the present disclosure.

FIG. 1 is a function block diagram of a circuit for liquid atomizing device of an embodiment of the present disclosure. Please refer to FIG. 1. A circuit for liquid atomizing device 1 includes a control unit 10, a voltage boosting unit 12, a conversion unit 14, a voltage adjustment unit 16 and an atomizing module 18. In practice, the control unit 10 is coupled to the voltage boosting unit 12 and the conversion unit 14. The voltage adjustment unit 16 is coupled between the conversion unit 14 and the atomizing module 18. The atomizing module 18 is contacted with or immersed in a liquid. When the voltage adjustment unit 16 of the present disclosure provides a driving voltage to the atomizing module 18, the atomizing module 18 produces a forward electrolysis reaction according to one of the electrolysis sections of the driving voltage. The atomizing module 18 produces a backward electrolysis reaction according to one of negative level sections of the driving voltage.

Moreover, the atomizing module 18 includes a first electrode and a second electrode. The first electrode and the second electrode of the atomizing module 18 dissociate the liquid according to the electrolysis sections of the driving voltage. For example, the first electrode is a positive electrode and the second electrode is a negative electrode. Therefore, negative ions or molecules dissociated from the liquid move toward the first electrode, and positive ions or molecules dissociated from the liquid move toward the second electrode. Next, the first electrode and the second electrode of the atomizing module 18 dissociate the liquid according to one of negative level sections of the driving voltage. The negative level sections indicate "the first electrode transforming into the negative electrode and the second electrode transforming into the positive electrode". Therefore, negative ions or molecules dissociated from the liquid move toward the second electrode, and positive ions or molecules dissociated from the liquid move toward the first electrode.

Simply speaking, the circuit for liquid atomizing device 1 of the present disclosure can enable the atomizing module 18 to produce the forward electrolysis reaction and the backward electrolysis reaction. The forward electrolysis reaction and the backward electrolysis reaction are abbreviated as a reversible electrolysis reaction. Therefore, the atomizing module 18 of the present disclosure does not just produce electrolysis material such as verdigris or other electrolysis material, by processing a unidirectional electrolysis. The circuit for liquid atomizing device 1 of the present disclosure can enable the atomizing module 18 to decrease the production of the electrolysis material. Therefore, the present disclosure can decrease the production of the electrolysis material to decrease the electrolysis material attached on the first electrode and the second electrode, whereby the usage life of the atomizing module 18 can be elongated. Naturally, the liquid atomizing device of the present disclosure is driven by frequency vibration to atomize the soluble drug liquid, for ensuring that mist having the drug grain size ranged from 3 μm to 5 μm can be absorbed by alveolus of human body.

For example, the control unit 10 is a control chip, a micro control chip or a PWM control chip, but this embodiment does not constrain the aspect of the control unit 10. The control unit 10 is built in multiple connection ports for outputting pulse modulation signals of which a frequency adjustment range is, for example, from 10 Hz to 1 MHz, and a duty cycle adjustment range is, for example, from 10% to 90%. In practice, the control unit 10 can output a first control signal C1 and a second control signal C2, the first control signal C1 and the second control signal C2 are used for controlling the voltage boosting unit 12 and/or the conversion unit 14, and the second control signal C2 is used for controlling the conversion unit 14.

For example, the voltage boosting unit 12 can be an adjustable boost converter or a regular boost converter. For example, the adjustable boost converter is a LTC3426 circuit manufactured by Linear Technology Corporation. For example, the regular boost converter is a HT77XXA series circuit manufactured by HOLTEK Semiconductor Inc. Simply speaking, the voltage boosting unit 12 is configured for boosting the voltage and outputting the boosted voltage to the conversion unit 14. This embodiment does not constrain the aspect of the voltage boosting unit 12.

The conversion unit 14 is configured for receiving the first control signal C1 and the second control signal C2 outputted by the control unit 10 and a voltage outputted by the voltage boosting unit 12. In practice, the conversion unit 14 includes, for example, a plurality of switches, an inductor and a diode D2. This embodiment does not constrain the aspect of the conversion unit 14. The conversion unit 14 is configured for amplifying the voltage outputted by the voltage boosting unit 12. For example, the conversion unit 14 receives the first control signal C1, and amplifies the voltage outputted by the voltage boosting unit 12 correspondingly. Simply speaking, the conversion unit 14 outputs a transforming voltage with respect to frequency vibration to the voltage adjustment unit 16 according to the first control signal C1 and the second control signal C2.

For example, the voltage adjustment unit 16 is an electrolytic capacitor, a multilayer ceramic capacitor, a tantalum capacitor, a clamp circuit or a clamp circuit having bias source. This embodiment does not constrain the aspect of the voltage adjustment unit 16. In practice, the voltage adjustment unit 16 is configured for adjusting the transforming voltage to output the driving voltage. The driving voltage includes a plurality of electrolysis sections and a plurality of negative level sections. The atomizing module 18 produces the forward electrolysis reaction according to one of electrolysis sections of the driving voltage. The atomizing module 18 produces the backward electrolysis reaction according to one of negative level sections of the driving voltage.

For example, a general circuit for liquid atomizing device does not have the conversion unit 14 and/or the voltage adjustment unit 16. Therefore, general atomizing module receives driving voltage having electrolysis sections larger than zero volt. Therefore, after the liquid atomizing device is frequently operated for a long time, the electrolysis material is produced on the first electrode and the second electrode of the general atomizing module. The electrolysis material will be attached on the first electrode and the second electrode of the general atomizing module after a long period of operation, and it causes the decayed usage life of the liquid atomizing device.

For example, the verdigris or other electrolysis material is produced on the first electrode and the second electrode of the general atomizing module.

However, the circuit for liquid atomizing device 1 of the present disclosure can adjust the transforming voltage to output the driving voltage having negative level sections. The driving voltage in one of negative level sections may enable the atomizing module 18 to produce the backward electrolysis reaction. Therefore, the speed of producing the electrolysis material on the first electrode and the second electrode of the atomizing module 18 can be decreased. Therefore, the atomizing module 18 can decrease the possibility of the electrolysis material being produced and attached on the first electrode and the second electrode, so that the usage life of the liquid atomizing device can be elongated.

It is worth noting that the driving voltage can be a square pulse voltage, a triangle pulse voltage or a sine pulse voltage. The driving voltage includes a plurality of electrolysis sections and a plurality of negative level sections. This embodiment does not constrain the aspect of the driving voltage. In practice, each electrolysis section indicates that the atomizing module 18 produces a forward electrolysis reaction, and each negative level section indicates that the atomizing module 18 produces a backward electrolysis reaction. The electrolysis sections indicate "the short circuit occurred between the first electrode and the second electrode of atomizing module 18 immersed within the liquid". To be specific, when the short circuit is occurred between the first electrode and the second electrode of the atomizing module 18, electrolysis current is generated between the first electrode and the second electrode, whereby the electrolysis material within the liquid can be dissociated. Therefore, the electrolysis material will be attached on the first electrode and the second electrode.

In addition, the atomizing module 18 may include an injection hole element and a piezoelectric actuating element. The injection hole element is provided with the piezoelectric actuating element. For example, the injection hole element can be a vibrating piece having a plurality of tiny through holes. For example, the piezoelectric actuating element is a piezoelectric piece for frequency vibration. The injection hole element and the piezoelectric actuating element may be a integratedly formed design or a combination design. This embodiment does not constrain the aspect of the atomizing module 18.

Next, the detailed circuit and operation of the circuit for liquid atomizing device are further illustrated.

Figure 2:
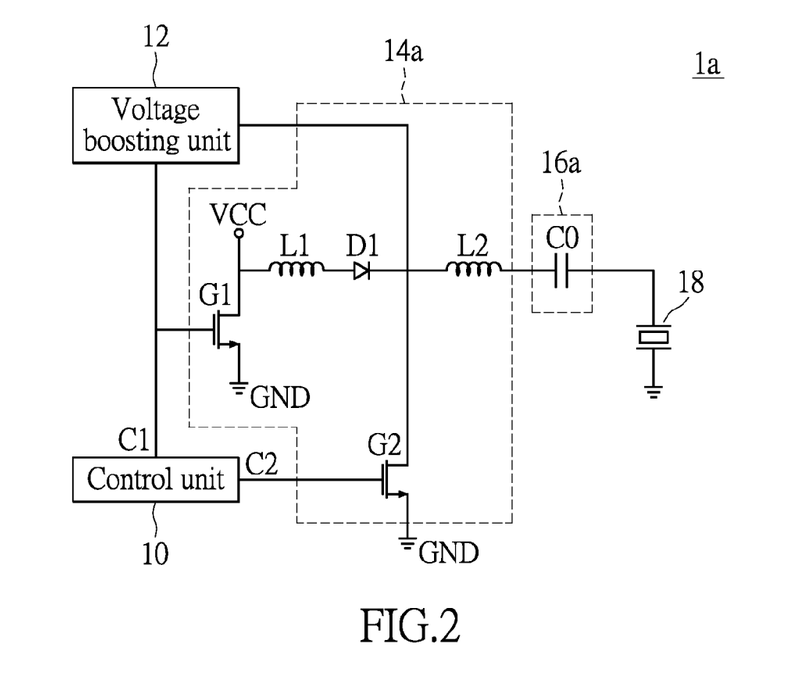
FIG. 2 is a schematic view of a circuit for liquid atomizing device of other embodiment of the present disclosure.

FIG. 2 is a schematic view of a circuit for liquid atomizing device of other embodiment of the present disclosure. Please refer to FIG. 2. For explanatory convenience, a capacitor is taken as an example for the voltage adjustment unit 16a of this embodiment. The capacitor is configured for adjusting the transforming voltage to the driving voltage. For example, the capacitor shifts the transforming voltage exceeding 0 volt to the driving voltage having negative level sections below 0 volt.

Next, the conversion unit 14 includes a first switch G1, a second switch G2, a first inductor L1, a second inductor L2, a unidirectional element D1 and a power source VCC. In practical application, a control end of the first switch G1 is coupled to the control unit 10. For example, a first end of the first switch G1 is the source end coupled to the first inductor L1 and the power source. A second end of the first switch G1 is a drain end coupled to a ground end GND. The first inductor L1 is coupled to an anode of unidirectional element D1 being a diode D2 in this embodiment. A cathode of the unidirectional element D1 is coupled to the second inductor L2, the voltage boosting unit 12 and a first end of the second switch G2. The second inductor L2 is coupled to the voltage adjustment unit 16a. A control end of the second switch G2 is coupled to the control unit 10. For example, the first end of the second switch G2 can be a source end coupled to the second inductor L2. The second end of the second switch G2 can be a drain end coupled to a ground end GND.

In detail, the control unit 10 can output a first control signal C1 and a second control signal C2. The first control signal C1 is used to control the conduction/cutoff of the first switch G1. The second control signal C2 is used to control the conduction/cutoff of the second switch G2. For example, the first switch G1 or the second switch G2 can be Metal-Oxide-Semiconductor Field-Effect Transistor (MOSFET), bipolar junction transistor (BJT), power transistor or gate transistor. For example, gate transistor can be a PMV213SN transistor manufactured by NXP Semiconductors. For example, the BJT can be a TIP33C transistor manufactured by STMicroelectronics. This embodiment does not constrain the aspect of the first switch G1 and the second switch G2.

It is worth mentioning that the voltage boosting unit 12 of this embodiment and the first inductor L1 and the unidirectional element D1 of the conversion unit 14 can be formed a boost converter. Those skilled in the art would realize that the first switch G1, the first inductor L1 and the unidirectional element D1 of the conversion unit 14 can be changed easily to form a boost converter which can replace the voltage boosting unit 12. Therefore, the control unit 10 can control the conduction/cutoff of the first switch G1 to enable the first inductor L1 to be charged or discharged. In addition, the control unit 10 can output the second control signal C2 to control the conduction/cutoff of the second switch G2, to enable the second inductor L2 to be discharged; or to enable the voltage of the voltage boosting unit 12 to charge the capacitor. This embodiment does not constrain the operation aspect of the circuit for liquid atomizing device 1a.

Figure 3A:
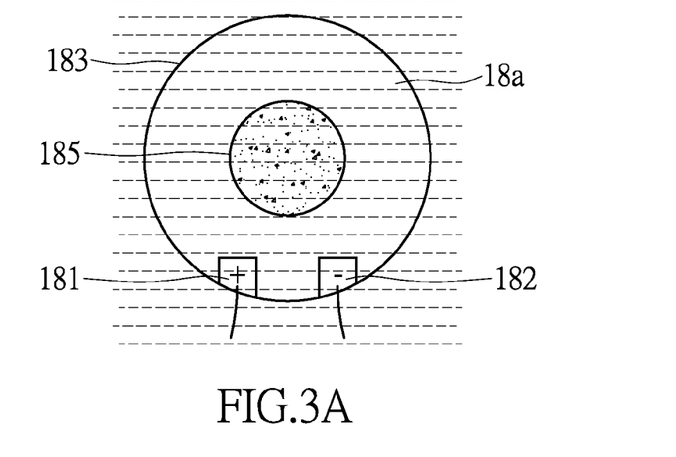
FIG. 3A is a schematic view of an atomizing module of the circuit for liquid atomizing device of the other embodiment of the present disclosure.
Figure 3B:
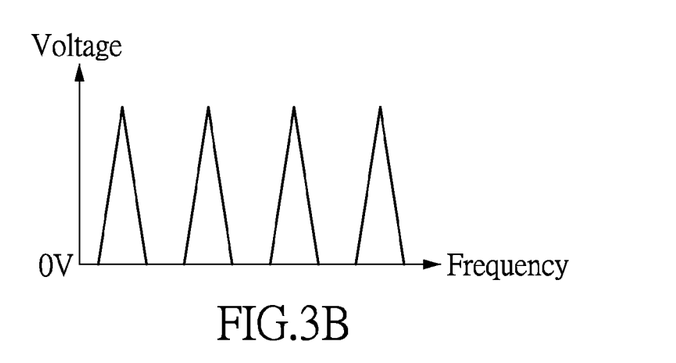
FIG. 3B is a waveform view of an input voltage of a voltage adjustment unit of the other embodiment of the present disclosure according to FIG. 2.
Figure 3C:
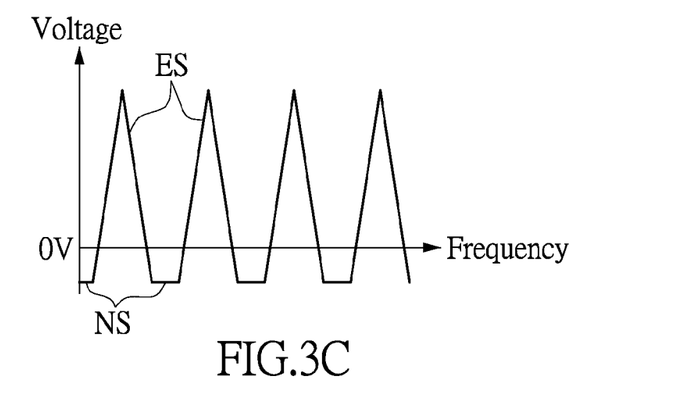
FIG. 3C is a waveform view of an output voltage of the voltage adjustment unit of other embodiment of the present disclosure according to FIG. 2.

FIG. 3A is a schematic view of an atomizing module of the circuit for liquid atomizing device of other embodiment of the present disclosure. FIG. 3B is a waveform view of an input voltage of a voltage adjustment unit of other embodiment of the present disclosure according to FIG. 2. FIG. 3C is a waveform view of an output voltage of the voltage adjustment unit of other embodiment of the present disclosure according to FIG. 2. Please refer to FIG. 3A, FIG. 3B, FIG. 3C and FIG. 2.

An atomizing module 18a is illustrated in FIG. 3A, the atomizing module 18a may include a piezoelectric actuating element 183 and an injection hole element 185. For example, the first electrode 181 and the second electrode 182 are welded on the same surface of the piezoelectric actuating element 183 and contacted with or immersed within the liquid. The atomizing module 18a produces an electrolysis reaction with the liquid according to the received driving voltage.

The waveform of the input voltage of the voltage adjustment unit 16a illustrated in the FIG. 3B is the voltage waveform of the transforming voltage outputted by the conversion unit 14a. For example, the voltage waveform of the transforming voltage can be a triangle pulse voltage, and all voltage values of the voltage waveform of the transforming voltage are larger than 0 volt.

The waveform of the output voltage of the voltage adjustment unit 16a illustrated in the FIG. 3C is also the voltage waveform of the driving voltage outputted by the voltage adjustment unit 16a. The voltage waveform of the driving voltage includes a plurality of negative level sections NS and a plurality of electrolysis sections ES. The piezoelectric actuating element 183 produces the forward electrolysis reaction with the liquid according to the driving voltage of one of the electrolysis sections ES. The piezoelectric actuating element 183 produces the backward electrolysis reaction with the liquid according to the driving voltage of one of the negative level sections NS. In addition, the piezoelectric actuating element 183 according to the driving voltage forms a sound wave oscillation to produce the effect of atomizing liquid.

It is worth mentioning that the voltage waveform of the driving voltage illustrated in FIG. 3C can be, for example, a triangle pulse voltage ranged from −6 volt to 17 volt, with 102 KHZ frequency, and the current is about 210 mA. Preferably, an absolute value of the positive voltage level is 17, and an absolute value of the negative voltage level is 6. The absolute value of the negative voltage level is smaller than the absolute value of positive voltage level. The absolute value of the positive level is triple of the absolute value of the negative voltage level. Simply speaking, the circuit for liquid atomizing device of the present disclosure utilizes lower electric power to drive the atomizing module 18a by frequency to form the sound wave oscillation.

Figure 4:
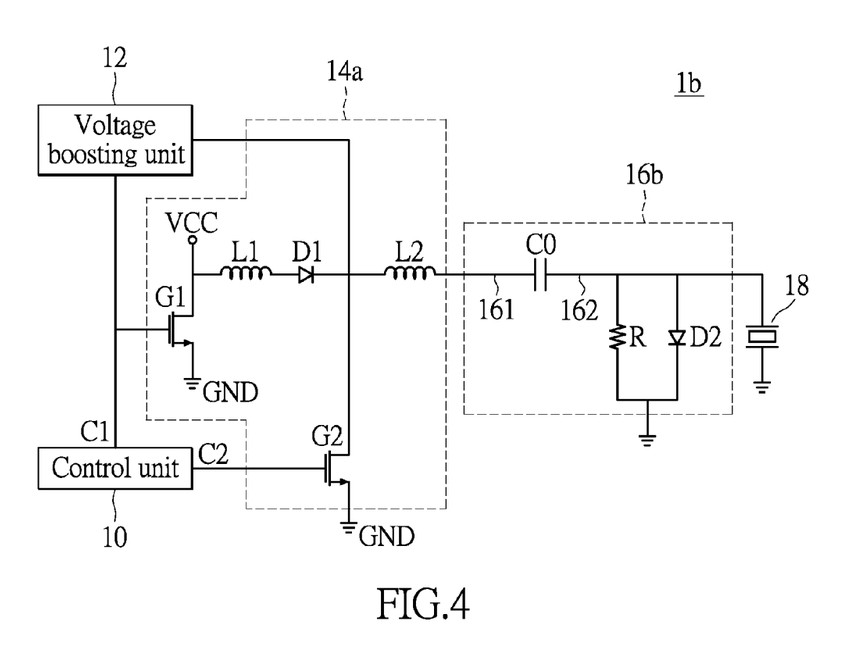
FIG. 4 is a schematic view of a circuit for liquid atomizing device of other embodiment of the present disclosure.

FIG. 4 is a schematic view of a circuit for liquid atomizing device of other embodiment of the present disclosure. Please refer to FIG. 4. The circuit for liquid atomizing device 1b of this embodiment is similar to the circuit for liquid atomizing device 1a of above-mentioned embodiment, for example, the circuit for liquid atomizing device 1b can also output a driving voltage having negative level section to the atomizing module 18. However, the difference between the circuit for liquid atomizing device 1b of this embodiment and the circuit for liquid atomizing device 1a of above-mentioned embodiment is that a voltage adjustment unit 16b of the circuit for liquid atomizing device 1b of this embodiment is a clamp circuit.

In detail, the clamp circuit includes a capacitor C0, a resistor R and a diode D2, and the capacitor C0 has a first side 161 and a second side 162. The first side 161 is coupled to the conversion unit 14a, and the second side 162 is coupled to the resistor R and the anode of the diode D2. The resistor R and the diode D2 are connected in parallel, the cathode of the diode D2 is coupled to the resistor R and a ground end GND, as shown in FIG. 4.

Naturally, the clamp circuit is configured for adjusting the transforming voltage to the driving voltage, to enable the atomizing module 18 to produce the reversible electrolysis reaction according to the driving voltage. Except the aforesaid difference, those skilled in the art would realize that the operation of this embodiment is substantially equivalent to the aforesaid embodiment, so it should be easily derivable for those skilled in the art after referring to the aforesaid embodiment and the difference, so the detailed description is omitted.

Figure 5A:
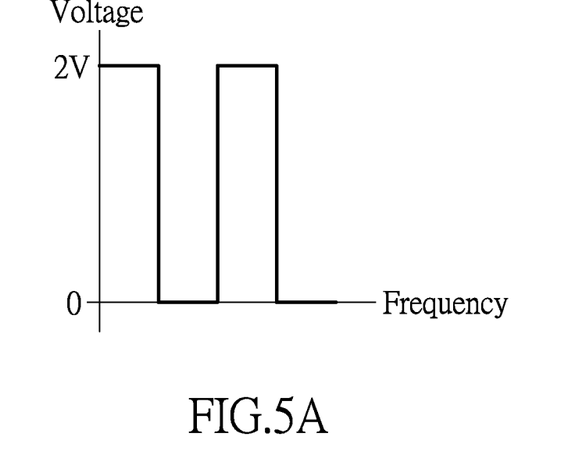
FIG. 5A is a waveform view of an input voltage of the voltage adjustment unit of other embodiment of the present disclosure according to FIG. 4.
Figure 5B:
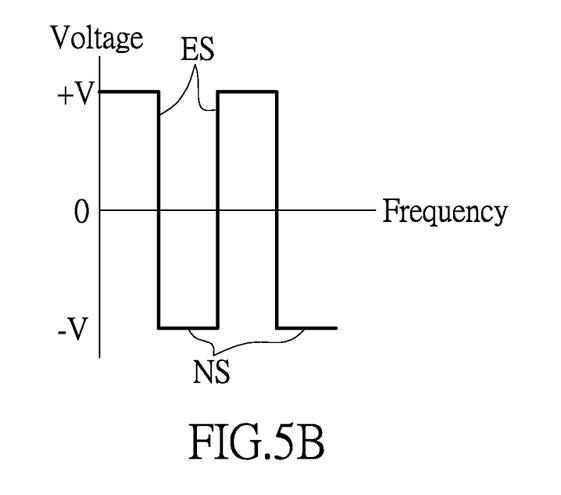
FIG. 5B is a waveform view of an output voltage of the voltage adjustment unit of the other embodiment of the present disclosure according to FIG. 4.

FIG. 5A is a waveform view of an input voltage of the voltage adjustment unit of other embodiment of the present disclosure according to FIG. 4. FIG. 5B is a waveform view of an output voltage of the voltage adjustment unit of other embodiment of the present disclosure according to FIG. 4. Please refer to FIG. 5A, FIG. 5B and FIG. 4.

The waveform of the input voltage of the voltage adjustment unit 16b illustrated in the FIG. 5A is also the voltage waveform of the transforming voltage outputted by the conversion unit 14a. For example, the voltage waveform of the transforming voltage can be a square pulse voltage, and voltage values of the voltage waveform example of the transforming voltage, for example, are 2V volt.

The waveform of the output voltage of the voltage adjustment unit 16b illustrated in the FIG. 5B is also the voltage waveform of the driving voltage outputted by the voltage adjustment unit 16b. The voltage waveform of the driving voltage includes a plurality of negative level sections NS and a plurality of electrolysis sections ES. For example, the voltage waveform of the driving voltage is a square pulse voltage ranged from −V volt to V volt. The piezoelectric actuating element produces the forward electrolysis reaction with the liquid according to the driving voltage of one of the electrolysis sections ES. The piezoelectric actuating element produces the backward electrolysis reaction with the liquid according to the driving voltage of one of the negative level sections NS. In addition, the piezoelectric actuating element according to the driving voltage forms a sound wave oscillation to produce the effect of atomizing liquid.

In addition, the voltage waveform of the driving voltage shown in FIG. 5B is a square pulse voltage ranged from −V volt to V volt. The absolute value of the positive voltage level is V. The absolute value of the negative voltage level is V. The absolute value of the negative voltage level is equal to the absolute value of positive voltage level. The voltage difference between the voltage wave crest and the voltage wave trough is still 2 volt. Simply speaking, the circuit for liquid atomizing device of the present disclosure drives the atomizing module 18 to form the sound wave oscillation without decreasing the amplitude of the driving frequency.

Figure 6:
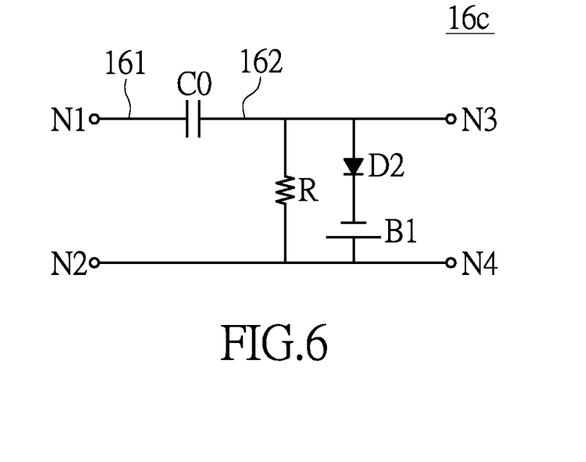
FIG. 6 is a circuit diagram of a voltage adjustment unit of other embodiment of the present disclosure.

FIG. 6 is a circuit diagram of a voltage adjustment unit of other embodiment of the present disclosure. Please refer to FIG. 6. The voltage adjustment unit 16c of this embodiment is similar to the voltage adjustment unit 16b of above-mentioned embodiment, for example, the voltage adjustment unit 16c can also output a driving voltage having negative level sections to the atomizing module 18. However, the difference between the voltage adjustment unit 16c of this embodiment and the voltage adjustment unit 16b of the above-mentioned embodiment is that the voltage adjustment unit 16c of this embodiment is a clamp circuit having a bias source B1.

In detail, a node N1 of the clamp circuit having the bias source B1 is coupled to the conversion unit 14. A node N3 is coupled to the atomizing module 18. Nodes N2 and N4 are coupled to a ground end GND. In practical application, the clamp circuit includes the bias source B1, a capacitor C0, a resistor R and a diode D2. Preferably, the bias source B1 is implemented by a battery or a storage battery. A negative electrode of the bias source B1 is coupled to a cathode of the diode D2, a positive electrode of the bias source B1 is coupled to the resistor R. The capacitor C0 has a first side 161 and a second side 162. The first side 161 is coupled to the conversion unit 14, and the second side 162 is coupled to the resistor R and the anode of the diode D2. The resistor R and the diode D2 are connected in parallel, the cathode of the diode D2 is coupled to the resistor R and a ground end GND, as shown in FIG. 6.

Naturally, the clamp circuit having the bias source B1 is configured for adjusting the transforming voltage to the driving voltage, to enable the atomizing module 18 to produce the reversible electrolysis reaction according to the driving voltage. Except the aforesaid difference, those skilled in the art would realize that the operation of this embodiment is substantially equivalent to the aforesaid embodiment, so it should be easily derivable for those skilled in the art after referring to the aforesaid embodiment and the difference, so the detailed description is omitted.

Figure 7A:
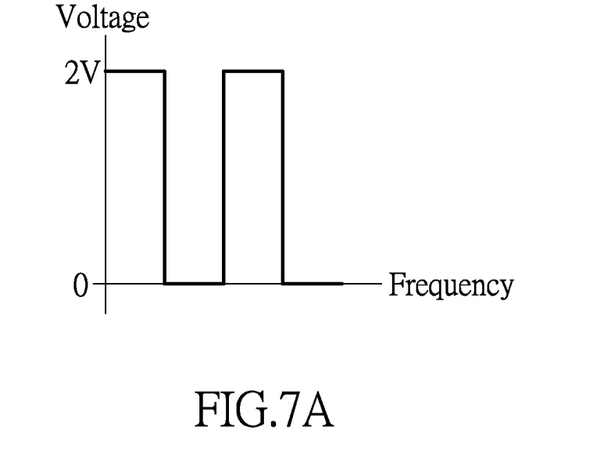
FIG. 7A is a waveform view of an input voltage of the voltage adjustment unit of other embodiment of the present disclosure according to FIG. 6.
Figure 7B:
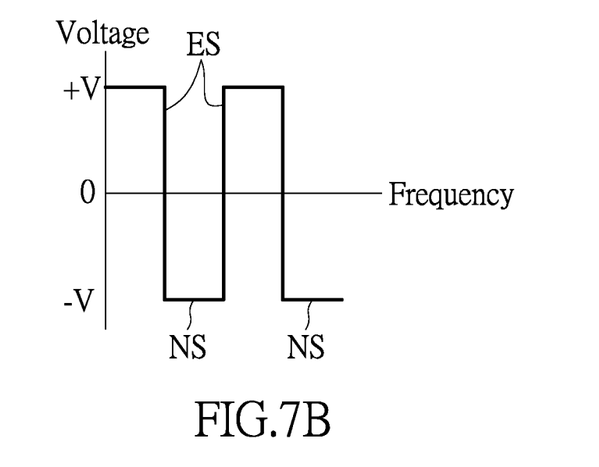
FIG. 7B is a waveform view of an output voltage of the voltage adjustment unit of other embodiment of the present disclosure according to FIG. 6.

FIG. 7A is a waveform view of an input voltage of a voltage adjustment unit of other embodiment of the present disclosure according to FIG. 6. FIG. 7B is a waveform view of an output voltage of the voltage adjustment unit of other embodiment of the present disclosure according to FIG. 6. Please refer to FIG. 7A, FIG. 7B and FIG. 6.

The waveform of the input voltage of the voltage adjustment unit 16c illustrated in the FIG. 7A is the voltage waveform of the transforming voltage outputted by the conversion unit 14a. For example, the voltage waveform of the transforming voltage can be a square pulse voltage, and voltage values of the voltage waveform of the transforming voltage, for example, are 2V volt.

The waveform of the output voltage of the voltage adjustment unit 16c illustrated in the FIG. 7B is also the voltage waveform of the driving voltage outputted by the voltage adjustment unit 16c. The voltage waveform of the driving voltage includes a plurality of negative level sections NS and a plurality of electrolysis sections ES. For example, the voltage waveform of the driving voltage is a square pulse voltage ranged from −V volt to V volt. The piezoelectric actuating element produces the forward electrolysis reaction with the liquid according to the driving voltage of one of the electrolysis sections ES. The piezoelectric actuating element produces the backward electrolysis reaction with the liquid according to the driving voltage of one of the negative level section NS. In addition, the piezoelectric actuating element according to the driving voltage forms a sound wave oscillation to produce the effect of atomizing liquid.

In addition, the voltage waveform of the driving voltage illustrated in FIG. 7B is a square pulse voltage ranged from −V volt to V volt. The absolute value of the positive voltage level is V, and the absolute value of the negative voltage level is V. The absolute value of the negative voltage level is equal to the absolute value of positive voltage level. The voltage difference between the voltage wave crest and the voltage wave trough is still 2 volt. Simply speaking, the circuit for liquid atomizing device of the present disclosure drives the atomizing module 18 to form the sound wave oscillation without decreasing the amplitude of the driving frequency.

To sum up, the present disclosure illustrates a circuit for liquid atomizing device in which a control unit controls a conversion unit to output a transforming voltage to a voltage adjustment unit. The voltage adjustment unit adjusts the transforming voltage to output a driving voltage to the atomizing module, to enable the atomizing module to produce the forward electrolysis reaction or the backward electrolysis reaction according to the electrolysis section or the negative level section of the driving voltage. By such design, the said circuit can prevent or decrease the production and attachment of the electrolysis material on the atomizing module, so that the usage life of the atomizing module can be elongated. Therefore, the circuit for liquid atomizing device of the present disclosure can certainly solve the problem of the electrolysis material being produced and attached on the atomizing module in prior art, and elongate the usage life of the liquid atomizing device.

The above-mentioned descriptions represent merely the exemplary embodiment of the present disclosure, without any intention to limit the scope of the present disclosure thereto. Various equivalent changes, alternations or modifications based on the claims of present disclosure are all consequently viewed as being embraced by the scope of the present disclosure.

What is claimed is:

1. A circuit for liquid atomizing device, adapted to control an atomizing module, the circuit comprising:
    a conversion unit;
    a control unit, coupled to the conversion unit and configured for controlling the conversion unit to output a transforming voltage; and
    a voltage adjustment unit, coupled between the conversion unit and the atomizing module;
    wherein the voltage adjustment unit according to the transforming voltage outputs a driving voltage to the atomizing module, the driving voltage includes a plurality of electrolysis sections and a plurality of negative level sections, and each of the electrolysis sections indicates that the atomizing module produces a forward electrolysis reaction, and each of the negative level sections indicates that the atomizing module produces a backward electrolysis reaction.

2. The circuit according to claim 1, wherein the voltage adjustment unit is a clamp circuit which comprises a capacitor, a resistor and a diode, and the capacitor has a first side and a second side, the first side is coupled to the conversion unit, the second side is coupled to the resistor and an anode of the diode, and the resistor and the diode are connected in parallel.

3. The circuit according to claim 2, wherein the clamp circuit further comprises a bias source, a negative end of the bias source is coupled to a cathode of the diode, and a positive end of the bias source is coupled to the resistor.

4. The circuit according to claim 1, wherein the voltage adjustment unit is an electrolytic capacitor, a multilayer ceramic capacitor or a tantalum capacitor.

5. The circuit according to claim 1, wherein the forward electrolysis reaction indicates that a first electrode and a second electrode of the atomizing module produce electrolysis reaction with liquid, negative ions dissociated from the liquid move toward the first electrode, and positive ions dissociated from the liquid move toward the second electrode.

6. The circuit according to claim 5, wherein the backward electrolysis reaction indicates that the first electrode and the second electrode of the atomizing module produce electrolysis reaction with the liquid, the negative ions dissociated from the liquid move toward the second electrode, and the positive ions dissociated from the liquid move toward the first electrode.

7. The circuit according to claim 5, further comprising a voltage boosting unit coupled to the control unit and the conversion unit, wherein the control unit outputs a first control signal and a second control signal, the conversion unit according to the first control signal to amplify the voltage outputted by the voltage boosting unit, the conversion unit according to the first control signal and the second control signal to output the transforming voltage with respect to frequency vibration to the voltage adjustment unit.

8. The circuit according to claim 1, wherein the conversion unit comprises:
    a first inductor;
    a second inductor, coupled to the voltage adjustment unit;
    a first switch, a control end of the first switch coupled to the control unit and the voltage boosting unit, a first end of the first switch coupled to the first inductor and a power source, a second end of the first switch coupled to a ground end;
    a second switch, a control end of the second switch coupled to the control unit, a first end of the second switch coupled to the second inductor, a second end of the second switch coupled to the ground end; and
    a unidirectional element, an anode of the unidirectional element coupled to the first inductor, a cathode of the unidirectional element coupled to the second inductor, the voltage boosting unit and the first end of the second switch.

9. A liquid atomizing device, comprising:
    a conversion unit;
    a control unit, coupled to the conversion unit and configured for controlling the conversion unit to output a transforming voltage;
    a voltage adjustment unit, coupled between the conversion unit and the atomizing module; and
    an atomizing module, coupled to the voltage adjustment unit and a ground end;

wherein the voltage adjustment unit according to the transforming voltage outputs a driving voltage to the atomizing module, the driving voltage includes a plurality of electrolysis sections and a plurality of negative level sections, and each of the electrolysis sections indicates that the atomizing module produces a forward electrolysis reaction, and each of the negative level sections indicates that the atomizing module produces a backward electrolysis reaction.

10. The liquid atomizing device according to claim 9, wherein the atomizing module comprises a piezoelectric actuating element configured for producing the forward electrolysis reaction according to the driving voltage of one of the electrolysis sections, and producing the backward electrolysis reaction according to the driving voltage of one of the negative level sections.

* * * * *